(12) United States Patent
Miller et al.

(10) Patent No.: US 11,376,442 B2
(45) Date of Patent: Jul. 5, 2022

(54) RELAY INTERFACE FOR CONNECTING AN IMPLANTED MEDICAL DEVICE TO AN EXTERNAL ELECTRONICS DEVICE

(71) Applicants: Scott Allan Miller, Lafayette, CO (US); Denis Dupeyron, Broomfield, CO (US)

(72) Inventors: Scott Allan Miller, Lafayette, CO (US); Denis Dupeyron, Broomfield, CO (US)

(73) Assignee: Cochlear Limited, Macquarie University (AU)

( * ) Notice: Subject to any disclaimer, the term of this patent is extended or adjusted under 35 U.S.C. 154(b) by 122 days.

(21) Appl. No.: 16/694,710

(22) Filed: Nov. 25, 2019

(65) Prior Publication Data
US 2020/0086121 A1 Mar. 19, 2020

Related U.S. Application Data

(60) Continuation of application No. 14/865,946, filed on Sep. 25, 2015, now Pat. No. 10,485,974, which is a
(Continued)

(51) Int. Cl.
*A61F 11/04* (2006.01)
*A61N 1/36* (2006.01)
(Continued)

(52) U.S. Cl.
CPC ..... *A61N 1/37247* (2013.01); *A61N 1/36038* (2017.08); *A61N 1/3787* (2013.01); *A61N 1/37264* (2013.01); *A61N 1/37282* (2013.01)

(58) Field of Classification Search
CPC ............ A61N 1/36032; A61N 1/37247; A61N 1/37264; A61N 1/37282; A61N 1/3787
(Continued)

(56) References Cited

U.S. PATENT DOCUMENTS

| | | | | |
|---|---|---|---|---|
| 4,441,210 A | * | 4/1984 | Hochmair | A61F 11/04 324/207.16 |
| 4,577,641 A | * | 3/1986 | Hochmair | A61F 11/04 381/60 |

(Continued)

FOREIGN PATENT DOCUMENTS

JP 60216695 A * 10/1995

OTHER PUBLICATIONS

Wikipedia, "Wireless Power", http://en.wikipedia.org/wiki/Wireless_power, retrieved Feb. 8, 2015 (Year: 2015).*
(Continued)

*Primary Examiner* — Erin M Piateski
(74) *Attorney, Agent, or Firm* — Pilloff Passino & Cosenza LLP; Martin J. Cosenza

(57) ABSTRACT

An interface relay system for use with a fully implantable medical devices that permits transcutaneous coupling of the implanted medical device to a consumer electronics device. In one embodiment, coupling the implanted medical device to the external electronics device provides a back-up source of power for operating the implanted medical device. In another embodiment, coupling the implanted medical device to the external electronics device allows for providing unidirectional and/or bidirectional data transfer between the devices. In one arrangement, the consumer electronics device may be connectable to a communications/data network to allow for network communication between the implantable medical device and a remote processing platform/server.

26 Claims, 12 Drawing Sheets

Related U.S. Application Data division of application No. 13/276,807, filed on Oct. 19, 2011, now Pat. No. 9,155,887.

(60) Provisional application No. 61/394,678, filed on Oct. 19, 2010.

(51) Int. Cl.
*A61N 1/372* (2006.01)
*A61N 1/378* (2006.01)

(58) Field of Classification Search
USPC .................................................. 607/57, 60
See application file for complete search history.

(56) References Cited

U.S. PATENT DOCUMENTS

| | | | | |
|---|---|---|---|---|
| 5,024,224 A * | 6/1991 | Engebretson | H04R 25/558 | 607/57 |
| 5,069,210 A * | 12/1991 | Jeutter | A61N 1/36038 | 607/57 |
| 5,085,628 A * | 2/1992 | Engebretson | H04R 25/606 | 381/337 |
| 5,531,774 A * | 7/1996 | Schulman | A61N 1/36038 | 607/57 |
| 5,569,307 A * | 10/1996 | Schulman | A61N 1/37252 | 607/57 |
| 5,571,148 A * | 11/1996 | Loeb | A61N 1/36038 | 607/57 |
| 5,603,726 A * | 2/1997 | Schulman | A61N 1/36185 | 607/57 |
| 5,609,616 A * | 3/1997 | Schulman | A61N 1/36038 | 607/56 |
| 5,702,342 A * | 12/1997 | Metzler | H04R 25/606 | 600/25 |
| 5,707,338 A * | 1/1998 | Adams | H04R 25/606 | 600/25 |
| 5,749,909 A * | 5/1998 | Schroeppel | A61N 1/3787 | 607/33 |
| 5,772,575 A * | 6/1998 | Lesinski | H04R 1/46 | 600/25 |
| 5,776,172 A * | 7/1998 | Schulman | A61N 1/36038 | 607/57 |
| 5,788,711 A * | 8/1998 | Lehner | H04R 25/606 | 623/10 |
| 5,795,287 A * | 8/1998 | Ball | H04R 25/502 | 600/28 |
| 5,842,967 A * | 12/1998 | Kroll | H04R 25/606 | 607/55 |
| 5,857,958 A * | 1/1999 | Ball | H04R 11/02 | 600/25 |
| 5,876,425 A * | 3/1999 | Gord | A61N 1/36038 | 607/57 |
| 5,879,283 A * | 3/1999 | Adams | H04R 25/606 | 607/57 |
| 5,899,847 A * | 5/1999 | Adams | H04R 1/46 | 607/55 |
| 5,938,691 A * | 8/1999 | Schulman | A61N 1/36038 | 607/57 |
| 5,954,628 A * | 9/1999 | Kennedy | H04R 25/606 | 607/57 |
| 5,991,663 A * | 11/1999 | Irlicht | A61N 1/36038 | 607/57 |
| 5,993,376 A * | 11/1999 | Kennedy | H04R 25/606 | 181/129 |
| 5,997,446 A * | 12/1999 | Stearns | A63B 21/4047 | 482/56 |
| 5,997,466 A * | 12/1999 | Adams | H04R 25/505 | 600/25 |
| 5,999,856 A * | 12/1999 | Kennedy | A61N 1/36039 | 607/57 |
| 6,001,129 A * | 12/1999 | Bushek | H04R 25/606 | 623/10 |
| 6,005,955 A * | 12/1999 | Kroll | H04R 25/606 | 381/328 |
| 6,067,474 A * | 5/2000 | Schulman | H02J 50/90 | 607/57 |
| 6,077,215 A * | 6/2000 | Leysieffer | H04R 25/606 | 600/25 |
| 6,154,023 A * | 11/2000 | Durand | G01R 1/07 | 324/117 R |
| 6,190,306 B1 * | 2/2001 | Kennedy | H04R 25/606 | 607/57 |
| 6,342,035 B1 * | 1/2002 | Kroll | H04R 25/606 | 607/57 |
| 6,390,970 B1 * | 5/2002 | Muller | H04R 25/604 | 600/25 |
| 6,398,717 B1 * | 6/2002 | Leysieffer | H04R 25/606 | 600/25 |
| 6,540,661 B1 * | 4/2003 | Muller | A61F 2/18 | 600/25 |
| 6,554,762 B2 * | 4/2003 | Leysieffer | H04R 25/407 | 600/25 |
| 6,603,860 B1 * | 8/2003 | Taenzer | H04R 25/606 | 381/328 |
| 6,620,094 B2 * | 9/2003 | Miller | H04R 25/606 | 607/57 |
| 6,651,501 B1 * | 11/2003 | Willis | H04R 29/001 | 381/60 |
| 6,712,754 B2 * | 3/2004 | Miller | H04R 25/30 | 623/10 |
| 6,788,790 B1 * | 9/2004 | Leysieffer | H04R 25/606 | 381/60 |
| 6,879,692 B2 * | 4/2005 | Nielsen | H04R 25/305 | 381/23.1 |
| 6,879,693 B2 * | 4/2005 | Miller | H04R 25/70 | 607/57 |
| 6,997,864 B2 * | 2/2006 | Conn | A61B 5/121 | 600/25 |
| 7,137,946 B2 * | 11/2006 | Waldmann | A61B 5/38 | 381/60 |
| 7,149,773 B2 * | 12/2006 | Haller | G16H 40/40 | 607/9 |
| 7,302,069 B2 * | 11/2007 | Niederdrank | H04R 25/70 | 381/60 |
| 7,447,319 B2 * | 11/2008 | Miller | H04R 25/30 | 381/60 |
| 8,503,703 B2 * | 8/2013 | Eaton | H04R 25/70 | 381/60 |
| 9,344,817 B2 * | 5/2016 | Eaton | H04R 25/554 | |
| 9,357,317 B2 * | 5/2016 | Eaton | H04R 25/70 | |
| 2003/0097037 A1 * | 5/2003 | Miller | H04R 25/606 | 600/25 |
| 2005/0010260 A1 * | 1/2005 | Gerber | A61N 1/36071 | 607/39 |
| 2005/0107831 A1 * | 5/2005 | Hill | A61N 1/40 | 607/2 |
| 2005/0143781 A1 * | 6/2005 | Carbunaru | A61N 1/37247 | 607/31 |
| 2006/0184212 A1 * | 8/2006 | Faltys | A61N 1/36039 | 607/57 |
| 2006/0190059 A1 * | 8/2006 | Griffith | A61N 1/36038 | 607/57 |
| 2007/0156204 A1 * | 7/2007 | Denker | A61N 1/3787 | 607/61 |
| 2007/0179565 A1 * | 8/2007 | Overstreet | A61N 1/36038 | 607/57 |
| 2008/0037798 A1 * | 2/2008 | Baechler | H04R 25/30 | 381/60 |
| 2008/0085023 A1 * | 4/2008 | Kulkarni | A61N 1/36038 | 381/320 |
| 2009/0118796 A1 * | 5/2009 | Chen | A61N 1/37229 | 607/60 |
| 2010/0145411 A1 * | 6/2010 | Spitzer | H04R 25/70 | 607/57 |
| 2010/0222847 A1 * | 9/2010 | Goetz | G16H 40/40 | 709/217 |

(56) References Cited

U.S. PATENT DOCUMENTS

2010/0232613 A1* 9/2010 Krause ............... A61N 1/37264
  381/60
2010/0254540 A1* 10/2010 Bang ..................... H04R 25/70
  381/317
2012/0095528 A1* 4/2012 Miller, III .......... A61N 1/37264
  607/57

OTHER PUBLICATIONS

Supplemental European Search Report for European application No. 11 835 077.6 dated Jul. 29, 2014. (Year: 2014).*

* cited by examiner

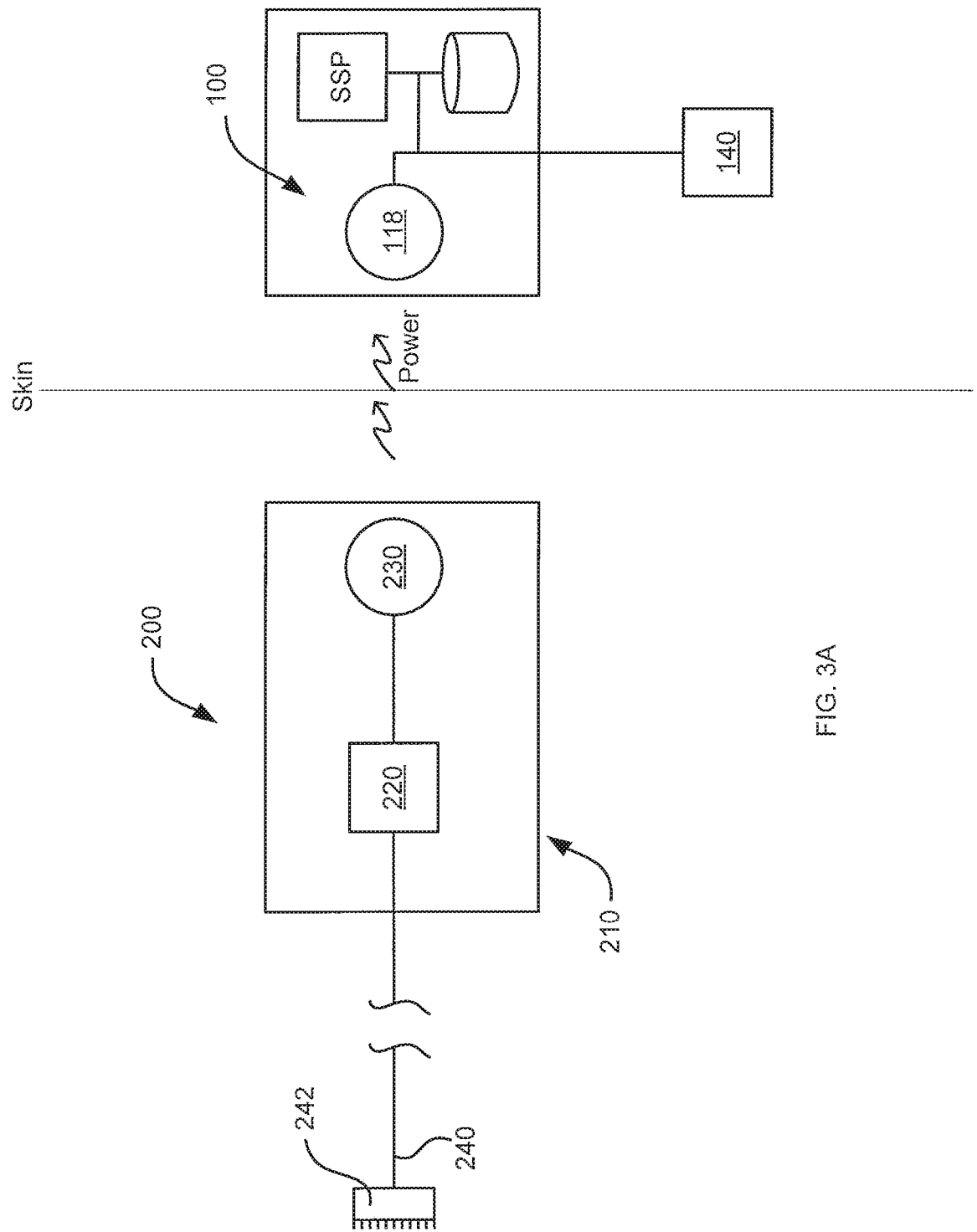

RELAY INTERFACE FOR CONNECTING AN IMPLANTED MEDICAL DEVICE TO AN EXTERNAL ELECTRONICS DEVICE

CROSS REFERENCE

The present application is a Continuation of U.S. patent application Ser. No. 14/865,946, filed Sep. 25, 2015, naming Scott Allan Miller as an inventor, which is a Divisional of U.S. patent application Ser. No. 13/276,807, filed Oct. 19, 2011, now U.S. Pat. No. 9,155,887, which claims priority to U.S. Provisional Patent Application No. 61/394,678, filed Oct. 19, 2010. This application claims priority to each of these applications, and the disclosures of each of these applications are hereby incorporated by reference herein in their entirety.

FIELD

The present disclosure relates to the field of implantable medical devices and implantable hearing instruments. In one aspect, an external relay interface is provided that allows interconnecting an implanted medical device to a consumer electronics device to provide, inter alia, back-up power for the implanted medical device and/or data communications between the implanted medical device and the consumer electronics device.

BACKGROUND

Implantable hearing aids stimulate internal components of the auditory system and are generally classified into one of two types, namely semi-implantable hearing aids and fully implantable hearing aids. In a semi-implantable hearing aid, some of the components, typically the microphone, power supply, and speech signal processor, are externally worn, while the transducer and key support functions are implanted within the auditory system. The externally worn portion and the implanted portion communicate transcutaneously to provide audio sound to the auditory system. In a fully implantable hearing aid, the entire device including the power supply, speech processor, microphone, and transducer are implanted subcutaneously.

Implanted hearing aids are typically used by individuals with significant loss of hearing function or damage to the auditory system. As a result, they differ in the manner by which the signal is processed and delivered to the patient. The processing step, known in the art as Speech Signal Processing ("SSP"), may include a number of steps such as amplification, frequency shaping, compression, etc. The steps in the SSP are determined by the design of the hearing aid, while the particular internal values used in the steps are generated from prescriptive parameters determined by an audiologist. Once a speech processor processes ambient acoustic signal, the altered signal is provided to an implanted transducer that stimulates the hearing impaired person's auditory system. The auditory stimulation may be done acoustically, mechanically, or electrically as a function of the type and severity of the hearing loss in the hearing impaired individual.

The Speech Signal Processing (SSP) may include a number of steps that are determined by the design of the hearing aid, while the particular internal values or fitting parameters used in the steps are generated from prescriptive parameters (PP) determined by the audiologist. For instance, the number of frequency bands used by a hearing aid are determined by the design, while the desired amount of attenuation of each frequency band is given as a prescriptive parameter, and the actual numbers used in the hearing aid to set these frequency attenuations are the internal values/fitting parameters.

In adapting a given hearing aid to a given patient, the various PP must be chosen to provide the most benefit to the patient, and are typically determined by a process known as fitting. This fitting process comprises determining various measures of the patient's hearing perception, generating the desired compensation as PP via a fitting algorithm, or simply algorithm. Continuing the fitting process, the PP are then converted to fitting parameters for the hearing aid, the hearing aid is programmed with these fitting parameters and then verifying that these fitting parameters demonstrably correspond to the desired PP. Once this is completed, the hearing aid is operated and various measures of the patient's aided hearing perception are determined to find out if the fitting process has been successful. If the patient's aided hearing perception is within acceptable limits the fitting is completed. Otherwise, the audiologist may elect to alter either the PP or the fitting parameters from the prescribed values slightly in order to attempt to improve the results for the patient.

The patient's hearing perception may be measured by subjecting the patient to various sound test protocols well known to those skilled in the art. These test protocols consist of sounds presented to the patient via speakers or headphones or in the case of implanted devices by direct application of an audio drive signal to an implanted transducer. The sounds may consist of tones, composite tones, multiple tones, speech, or the like, and they may be presented to one or both of the ears. For example, a common measurement of a patient's hearing perception is to subject the patient to a sequence of pure tones at specific "audiometric" frequencies. A device known as an audiometer is typically used to generate this sequence of tones as electrical signals which are thence conducted by a cable to the speakers or headphones. These tones are presented to the subject at various amplitudes according to specific protocols used in the industry.

Once the appropriate audiometric measures are performed, a fitting algorithm is used to convert this data into the most appropriate mapping between the patient's hearing and normal hearing. This process is not as simple as it sounds as various schools of thought exist as to the best fitting algorithms, and the range of their applicability. The results of the algorithm is a set of mapping parameters describing how to map the acoustic input into the patient's perception as prescriptive parameters. Typically, calculations of the algorithm are computationally complex resulting in significant waiting times during fitting.

Once this is done, the prescriptive parameters must be converted into parameters suitable for use inside of the hearing aid. Depending on the technology used in the speech signal processing, this results in numbers, here called internal values or fitting parameters, which are then programmed into the hearing aid. This function is often included in the function of the fitting software.

After the operation of the hearing aid is confirmed, the appropriate internal values are programmed into the hearing aid, and the device is once again operated and analyzed. The expected performance of the desired program is then confirmed by comparing the actual response of the programmed device with the desired performance. This confirms that the patient will be receiving at least approximately the desired amount of hearing compensation by the aid, will not be subjected to an excessive amount of acoustic energy, and that the performance of the aid will be suitable to warrant further tests with the patient.

If, as occasionally happens, the actual response of the device as determined by the hearing aid analyzer is different from the desired response by a significant amount, the audiologist may elect to adjust the programmed internal values, or somewhat equivalently, the prescriptive parameters. This may necessitate repeating the above-noted process. Accordingly, the fitting procedure may be quite time consuming.

SUMMARY

Provided herein are systems and methods (i.e., utilities) that allow for interconnecting a fully implantable medical device to an external unit. More specifically, a coupling device allows for connecting an implanted medical device to a consumer electronic device such as, for example and without limitation, a cell phone, laptop, tablet computer, or other such device. Such connection may provide a number of independent benefits. For instance, in one arrangement, such connection may allow for utilizing power in the consumer electronic device as a back-up power source for the implanted medical device. In another arrangement, connection to such a consumer electronic device may provide a means for sending and/or receiving data communications to/from the implanted medical device as well as in various instances to/from a data network. In such an arrangement, one or more settings or parameters of the implantable medical device may be altered utilizing the consumer electronic device and/or via a remote platform communicating through the consumer electronic device.

According to a first aspect, an external device is provided for transcutaneously connecting a consumer electronics device with an implanted medical to power the implanted medical device. The device includes a housing adapted for external mounting proximate to the implanted medical device. A cable extends from this housing and terminates in a connector that is adapted for receipt within a port of a consumer electronics device. At least a first terminal of this connector is connectable to a power source of the consumer electronics device. Also disposed within the housing is power control circuitry that is operable to receive power from the first terminal (i.e., via the cable) and adapt that power for transcutaneous transmission to the implanted medical device. Accordingly, to provide such transcutaneous transmission, the device includes a wireless transmitter for transmitting power from the housing to a receiver of the implanted medical device. In one arrangement, this wireless transmitter is an inductive coupling where the internal device and implanted device each include a coil. In other arrangements, an RE coupling may be utilized where such an implanted medical device may include a receiver and rectifying circuitry.

The power control circuitry within the external device may include an inverter for converting DC current received from the first terminal to AC current, which may allow for its transcutaneous transmission. Further, the power control circuitry may modulate a first electrical signal received by the first terminal to generate a second electrical signal for wireless transmission to the implantable medical device. In such an arrangement, one or more parameters of the first electrical signal might be altered for compatibility with the implanted medical device. Such parameters include, without limitation, voltage and amperage.

In a further arrangement, a second terminal of the connector is adapted to receive data signals originating from the consumer electronics device. In such an arrangement, the housing may further include a controller or microcontroller (e.g., microprocessor) that is operable to process the data signals received via the connector and generate processed signals for transmission (e.g., via the wireless transmitter) to the implanted medical device. In a further arrangement, the controller is operative to receive signals originating from the implanted medical device and generate an output signal that is provided to at least one terminal of the connector. Accordingly, this output signal may be provided to the consumer electronic device.

The housing may further include one or more electronic memory devices (such as, without limitation, EEPROM, etc.) that allows the device to store, for example, communication protocols that allow for communication between the implanted medical device and one or more consumer electronic devices. In such an arrangement, signals received from the consumer electronic device may be translated to a protocol that is compatible with the implanted medical device. Likewise, signals originating from the medical device may be translated to be compatible with one or more different consumer electronic devices.

In a further aspect, a system for interconnecting an implanted medical device to a communications network is provided. The utility includes an implant interface device including a housing that is adapted for external mounting proximate to an implanted medical device. A cable extending from the housing terminates in a connector that is adapted for connection with a mating port. Finally, the implant interface device includes a wireless transceiver for transcutaneously transmitting power and/or data received via the connector to an implanted medical device as well as transcutaneously receiving communications from the implanted medical device. The utility further includes a portable consumer electronics device that includes a power source, a processor, and a communications port that is adapted to receive the connector of the implant interface device. Finally, the consumer electronics device further includes an interface for interconnecting the consumer electronics device to a communications network. Accordingly, the consumer electronics device is operative to transmit data originating from the medical device to the communication network and vice versa. As will be appreciated, the consumer electronics device may include computer-readable medium on which protocol and/or logic is included for providing communications to/from the medical device.

In one arrangement, the portable consumer electronics device is a mobile phone. In such an arrangement, the mobile phone may provide, in addition to interconnection to a data network, power for the implanted medical device and/or audio signals. In the latter regard, it will be appreciated that the mobile phone may include a microphone adapted to receive ambient audio signals. Accordingly, these ambient audio signals may be transferred to an implanted hearing instrument. Such functionality may allow a wearer of an implanted hearing instrument to utilize an external microphone to provide directionality and/or improved signal receipt in, for example, noisy situations. In such an arrangement, the cable between the implant interface device and the consumer electronics device may be of sufficient length to allow the user to place the device nearer to a desired audio source (e.g., for instance, in the middle of a table at a restaurant).

In another arrangement, the consumer electronics device may be a tablet computer or laptop computer. In such an arrangement, the connecting port may be a USB or mini USB cable that allows for power and/or data communications between the implant interface device. In such an arrangement, the tablet and/or laptop computer may provide wireless communication with the data network (e.g., internet) and/or hardwired communication to a data network (e.g., WAN, LAN, etc.).

In any arrangement, it will be appreciated that the ability of the consumer electronics device to interconnect to a communications network allows for transmitting data from the implanted medical device to a remote location. Accordingly, this data may be processed remotely, which may allow for, inter alia, increased processing power to be applied to data parameters received from the implanted medical device. In the case of an implanted hearing instrument, this may allow for providing improved fitting parameters for the device as well as providing operating upgrades (e.g., speech software processing algorithms) upon development. In this regard, a user of such an instrument may not necessarily have to travel to see an audiologist each time an upgrade is available for their instrument.

According to another aspect, a utility is provided for use with an implantable hearing instrument. The utility includes establishing a wireless connection with implanted hearing instrument using an external interface device where the external interface device includes a wireless transmitter adapted to communicate with a wireless transmitter/receiver of the implanted hearing instrument. The external interface device is connected to a consumer electronics device (e.g., directly or via a second wireless interface), which is connectable to a communications network via a network interface. The consumer electronics device is operative to transmit data parameters to a platform in the communications and/or data network where the data parameters are transcutaneously obtained from the implantable hearing instrument. Likewise, the electronics device is operative to receive fitting parameters via the data network interface that are generated in response to the provided parameters. These received fitting parameters may be transmitted to the implantable hearing instrument to upgrade the operation thereof.

In addition, one or more audiological functions may be provided by the consumer electronics device. For instance, the consumer electronics device may be operative to output one or more series of tones that may be utilized to generate data parameters by the implanted hearing instrument. In such an arrangement, the utility may be operative to iteratively obtain data parameters from the implanted hearing instrument, send those for remote processing, receive fitting parameters, and retest the new fitting parameters. Accordingly, the system may allow for improved fitting.

According to another aspect, a utility is provided where a consumer electronics device is utilized to alter the operation of implanted medical device. According to this aspect, a consumer electronics device is interconnected to an interface device that permits the consumer electronics device to communicate with implanted medical device. In this regard, the interface device and/or the consumer electronics device may include protocol that allows for communication between the consumer electronic device and the implanted medical device. The consumer electronics device also supports an application that provides a graphical user interface on a display output of the consumer electronics device. In one arrangement, a control interface screen provided on the display output that allows a user to alter the operation of the implanted hearing instrument. In this regard, the user interface permits a user to provide one or more inputs that allow for altering the operation of the implantable medical device.

In a further arrangement of the present aspect, a consumer electronics device also provides the ability to connect to a communications and/or data network. In this arrangement, the control interface screen may correspond to a webpage or other interactive page associated with remote server. In this regard, user inputs directed to altering the control of the implanted hearing instrument may be provided to a remote server for subsequent processing. Such a remote server may provide control information for altering functionality of the implanted medical device. In the case of an implanted hearing instrument, functionality associated with remote server may include fitting algorithms and/or pre-stored user settings. In the latter regard, a user may store settings that are applicable to different use environments. Accordingly, the user may access these pre-stored settings and download them from the server via the consumer electronic device as needed. In the former regard, the remote server may allow for adjustments of fitting settings and/or new fitting of the implanted hearing instrument. In this regard, the control interface screen may provide multiple different inputs relative to control the settings of the implantable hearing instrument. Furthermore, the remote server may provide, via the consumer electronic device, one or more control and/or test signals that may be provided to the implantable hearing instrument for testing/fitting purposes. Accordingly, upon outputting such a test signal, the implanted hearing instrument and/or user a user may provide feedback to the remote server, via the consumer electronics device for additional processing.

In a further arrangement, the control interface screen and/or consumer electronic device may provide communications (e.g., textual and/or audio) with a medical technician (e.g., audiologist). In this regard, a user may communicate with a trained technician while adjusting their implanted medical device. Such communication via the consumer electronics device may be performed in conjunction with communication with the remote server.

In another aspect, a utility is provided for accumulating information from implantable medical devices and storing this information in a location accessible via a data network such that this information may be utilized in subsequent fitting and/or adjustment of such implantable medical devices. In one arrangement, information associated with the settings of implantable hearing instruments and/or information regarding the condition of the patients utilizing those instruments is stored in a database such that this information may be accessed via a data network. Further, such information may be stored in a multivariate database such that multivariate statistical analysis may be performed on the information to identify trends and/or commonalities therein. In this regard, upon receiving a request for a fitting or adjusting of a similar implantable hearing instrument, information associated with the requesting user and/or a current response of the implantable hearing instrument of the requesting user (i.e., to a known stimulation) may be utilized to identify settings of implantable hearing instruments having similar conditions. That is, one or more fitting parameters/settings may be identified and/or suggested based on prior settings of other users. Accordingly, upon finalizing the fittings/settings and/or adjustment of the requesting user, such information may be added to the database.

BRIEF DESCRIPTION OF THE DRAWINGS

For a more complete understanding of the present invention and further advantages thereof, reference is now made to the following detailed description taken in conjunction with the drawings in which:

FIG. 3A illustrates internal components of one embodiment of a relay interface.

DETAILED DESCRIPTION

Reference will now be made to the accompanying drawings, which at least assist in illustrating the various pertinent features of the presented inventions. In this regard, the following description of a fully implantable hearing instrument is presented for purposes of illustration and description. Furthermore, the description is not intended to limit the inventions to the forms disclosed herein. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications required by the particular application(s) or use(s) of the presented inventions.

Figure 1A:
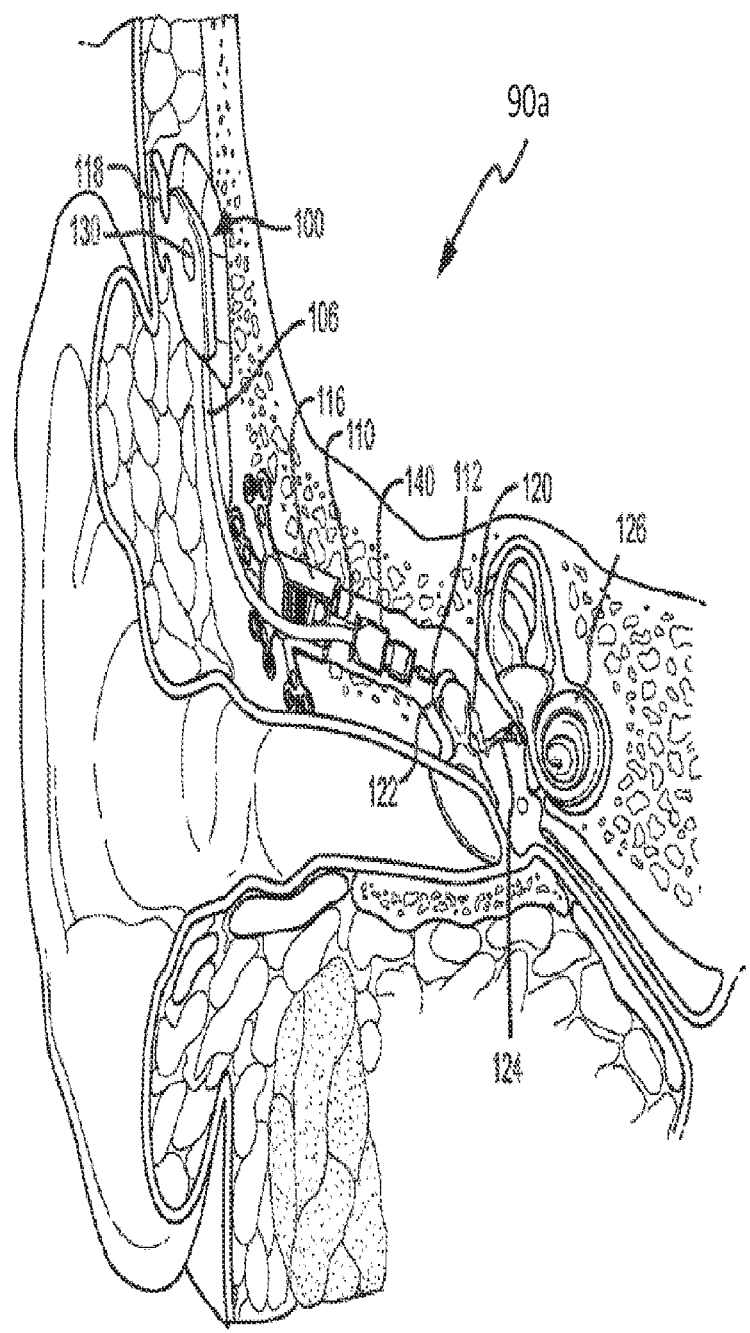
FIG. 1A illustrates one embodiment of an implanted hearing instrument.
Figure 1B:
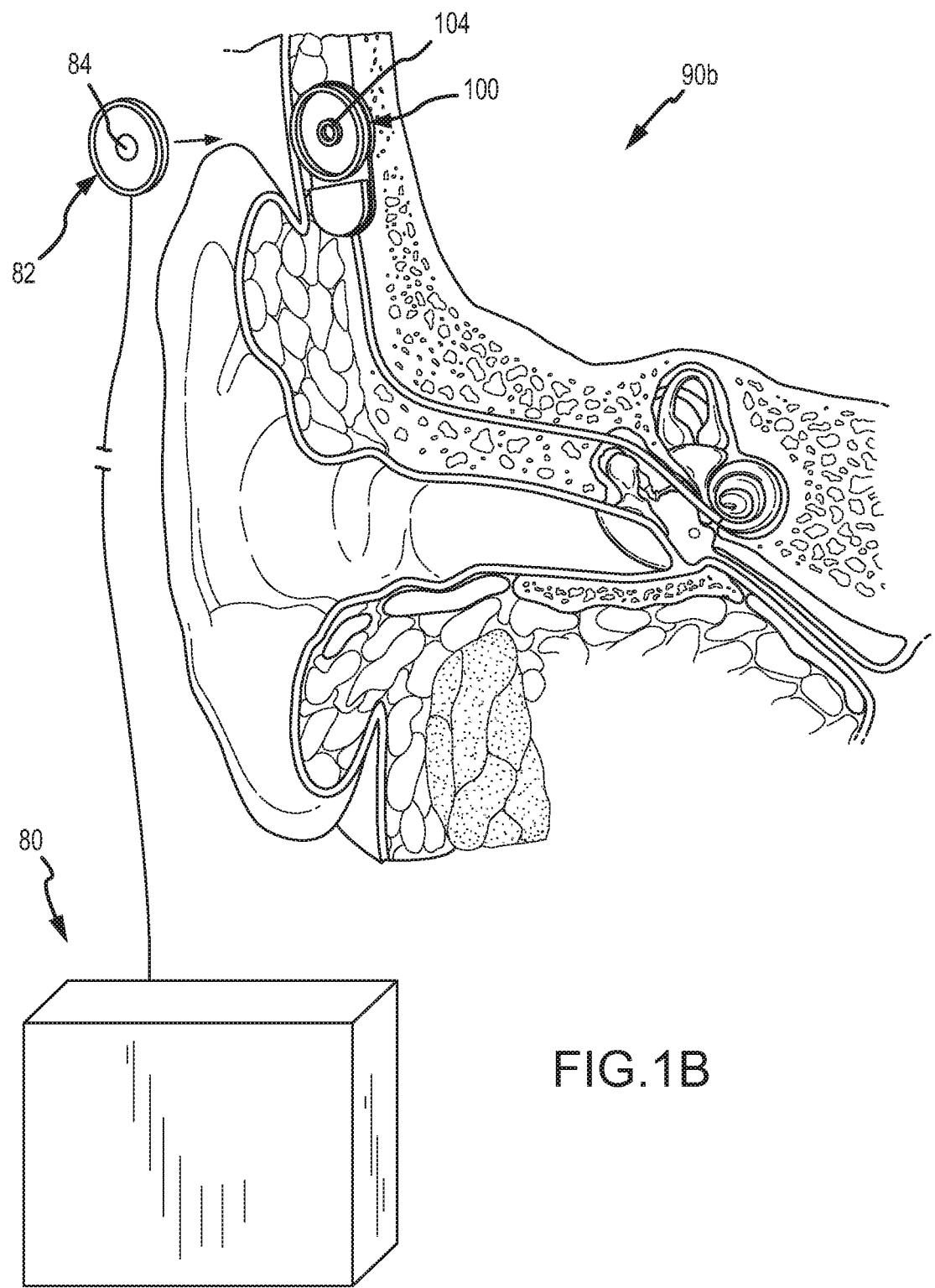
FIG. 1B illustrates another embodiment of an implanted hearing instrument.

FIG. 1A illustrates one application of the present invention. As illustrated, the application comprises a fully implantable middle ear hearing instrument 90a. As will be appreciated, certain aspects of the present invention may be employed in conjunction with 90a other implantable hearing instruments such as a cochlear stimulation system 90b, as illustrated in FIG. 1B, a bone actuated hearing instrument, as well as other implantable medical devices, and therefore the illustrated application is for purposes of illustration and not limitation.

In the illustrated system of FIG. 1A, a biocompatible implant housing 100 is located subcutaneously on a patient's skull. The implant housing 100 includes a signal receiver 118 (e.g., comprising a coil element) and a microphone 130 that is positioned to receive acoustic signals through overlying tissue. The implant housing 100 may be utilized to house a number of components of the fully implantable hearing instrument. For instance, the implant housing 100 may house an energy storage device, a microphone transducer, and a signal processor. Various additional processing logic and/or circuitry components may also be included in the implant housing 100 as a matter of design choice. Typically, the signal processor within the implant housing 100 is electrically interconnected via wire 106 to an electromechanical transducer 140.

The transducer 140 is supportably connected to a positioning system 110, which in turn, is connected to a bone anchor 116 mounted within the patient's mastoid process (e.g., via a hole drilled through the skull). The transducer 140 includes a connection apparatus 112 for connecting the transducer 140 to the ossicles 120 of the patient. In a connected state, the connection apparatus 112 provides a communication path for acoustic stimulation of the ossicles 120, e.g., through transmission of vibrations to the incus 122.

During normal operation, acoustic signals are received subcutaneously at the microphone 130. Upon receipt of the acoustic signals, a signal processor within the implant housing 100 processes the signals to provide a processed audio drive signal (e.g., a transducer drive signal) via wire 106 to the transducer 140. As will be appreciated, the signal processor may utilize digital processing techniques to provide frequency shaping, amplification, compression, and other signal conditioning, including conditioning based on patient-specific fitting parameters. The audio drive signal causes the transducer 140 to transmit vibrations at acoustic frequencies to the connection apparatus 112 to effect the desired sound sensation via mechanical stimulation of the incus 122 of the patient. These vibrations are then transmitted from the incus 122 to the stapes 124, effecting a stimulation of the cochlea 126.

To power the fully implantable hearing instrument system of FIG. 1A or 1B, an external charger unit 80 (see FIG. 1B) may be utilized to transcutaneously re-charge an energy storage device within the implant housing 100. In this regard, a coupling element 82 of the external charger unit 80 may be configured for disposition behind the ear of the implant wearer in alignment with the implant housing 100. The coupling element 82 of external charger unit and the implant housing 100 may each include one or more magnets 84, 104, respectively to facilitate retentive juxtaposed positioning. Such an external charger unit may include a power source and a transmitter located in the coupling element 82 that is operative to inductively couple with the implant housing 100 transcutaneously. Typically, such recharging is done at night. Further, the on-board storage device of the implantable hearing instrument is typically sized to provide operating power for the system for at least an entire waking day.

Use of such fully implantable hearing instruments can present various difficulties to users. For instance, while onboard power supply of the implantable instruments are typically sized to provide one or more days of continuous use without recharge, there can be instances when a user fails to recharge their unit and desires a backup power source. Further, adjusting a fully implantable hearing instrument typically requires an in-depth fitting process where a user must travel to an audiologist having specialized equipment that allows the audiologist to communicate with the implanted hearing instrument and obtain information from the unit in order to generate new and/or alter existing fitting parameters. It is against this background that various aspects of the presented inventions are provided.

Relay Interface

Figure 2:
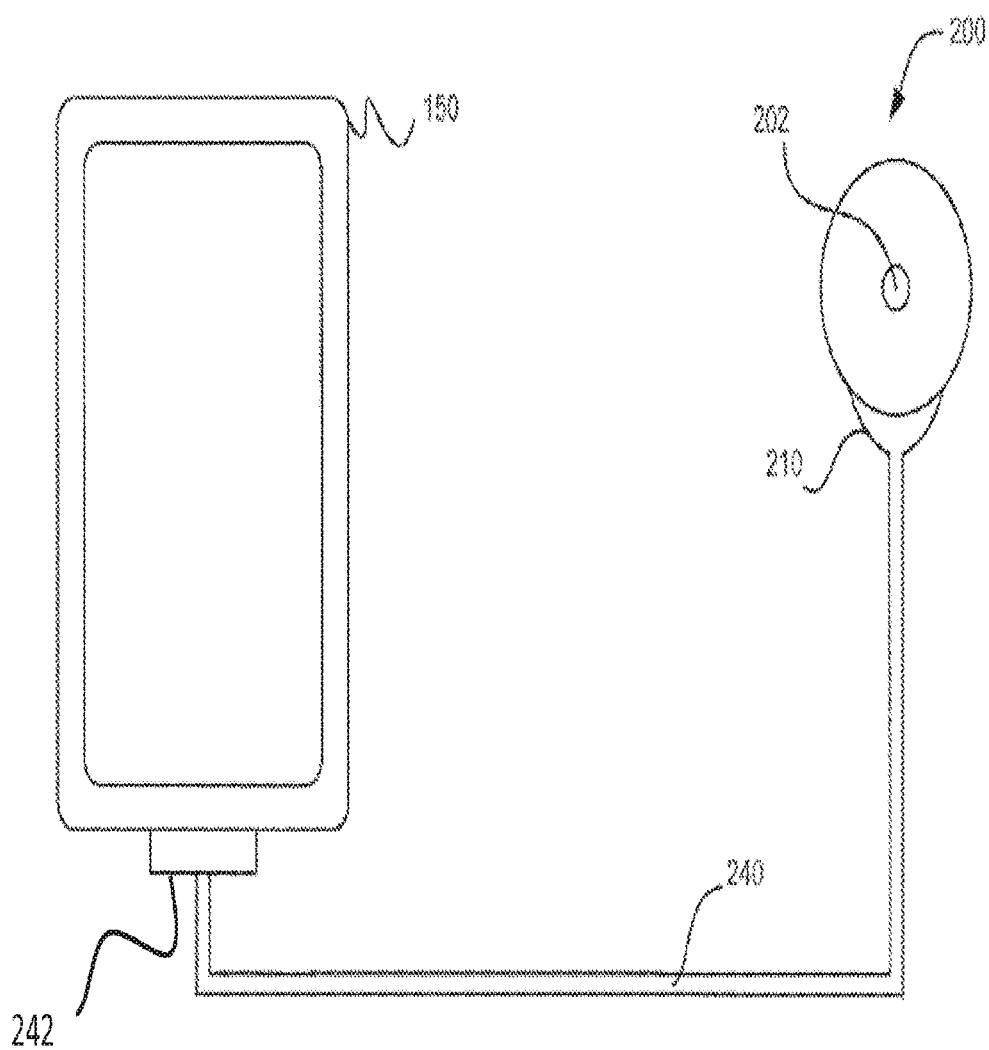
FIG. 2 illustrates one embodiment of a relay interface interconnected to a consumer electronic device.
Figure 3B:
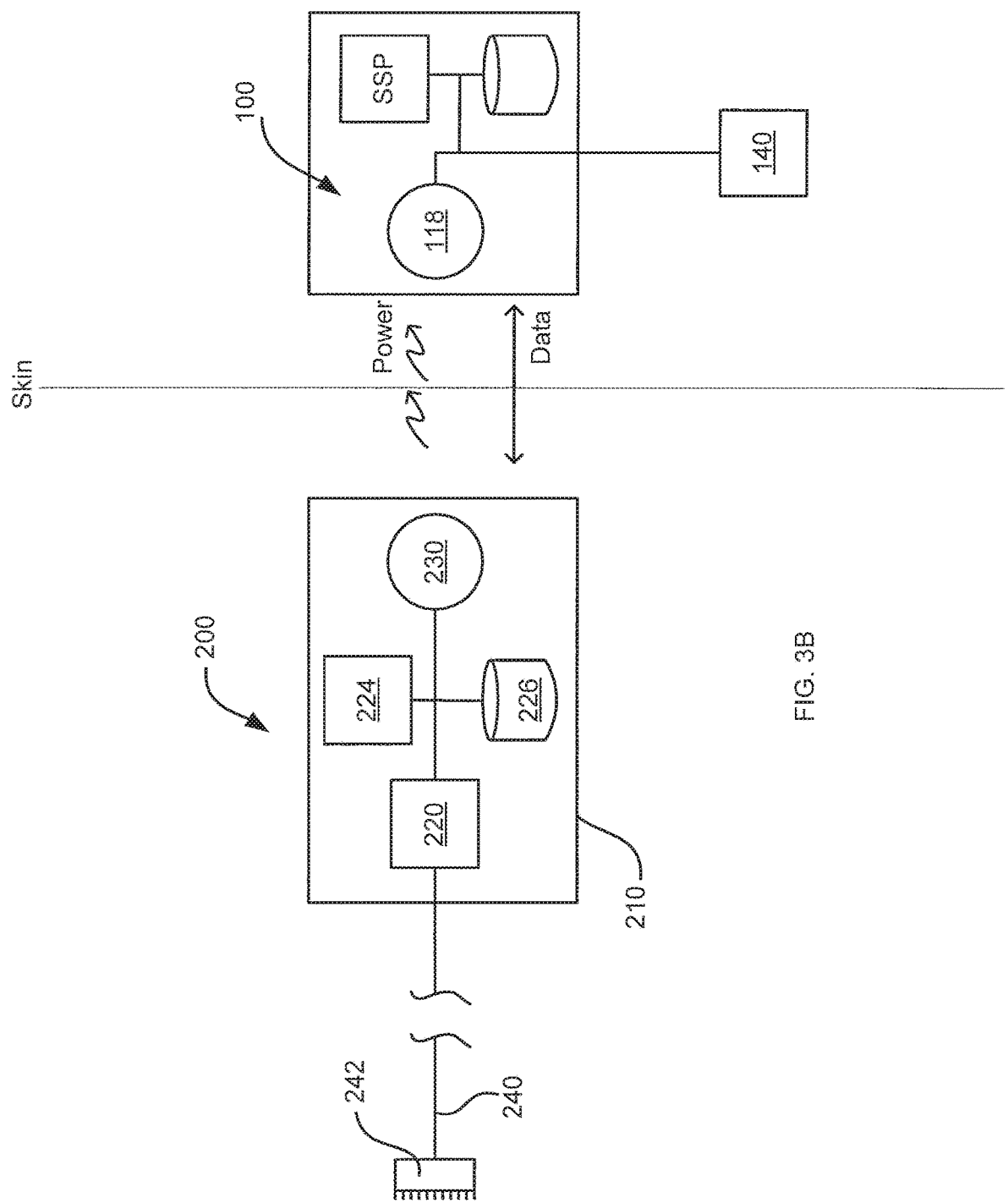
FIG. 3B illustrates internal components of another embodiment of a relay interface.

FIG. 2 illustrates one embodiment of a relay interface 200 that allows the user of an implanted hearing instrument, or other implanted medical device, to interconnect the implanted medical device to a consumer electronic device. In this regard, the consumer electronic device may be utilized to provide operating power to the implanted medical device. That is, rather than providing a specialized backup power source, the relay interface allows the user to interconnect to one or more different consumer electronic devices that have a power source, which may be utilized to provide backup power when necessary, Along these lines, it has been recognized that a majority of the population now regularly carries a consumer electronic device that includes a power source, Specifically, a majority of the population own and tend to have ready access to a mobile phone, which includes a power source. Accordingly, it has been determined that, by providing a relay interface that allows for connection with such a consumer electronic device, users of an implanted medical device may have access to backup power without having to carry a specialized power source (e.g., battery pack). Further, it has been recognized that the ability to interconnect such an interface to a consumer electronic device such as a mobile phone or laptop computer also provides the ability to interconnect the medical device to a communications network, which may allow, inter alia, adjustment of the implanted medical device remotely and/or remote diagnosis and/or fitting As illustrated in FIG. 2, the relay interface 200 includes a housing 210 that houses, at a minimum, power control circuitry 220, a transmitter/receiver 230 and a cable 240 that extends from the relay interface and terminates in a connector 242, which is adapted for receipt within a port of a consumer electronic device. See FIG. 3A. Commonly, the relay interface will further include a controller 224, e.g., microprocessor, and/or electronic storage media 226. See FIG. 3B. Typically, the electronic storage media 226 is nonvolatile such that power is not required to maintain, for example, operating instructions or other protocol stored therein. In one arrangement, EEPROM memory is utilized. However, this is not a requirement. The transmitter/receiver 230 is operative to inductively couple with the signal receiver 118 of the implanted medical device. Through such transcutaneous coupling, the transmitter/receiver 230 is operative to provide power to the implanted medical device and/or send and receive data communications there between. The housing 210 also typically includes one or more magnets 202 that provide means to position the relay interface relative to the implanted housing 100 of the implantable hearing instrument. However, it will be appreciated that in other embodiments clips may be utilized to position the relay interface behind the ear.

In one arrangement, the relay interface 200 is a passive device that contains no internal power source. See FIG. 3A. In this arrangement, the relay interface relies on a power source from an interconnected consumer electronics device 150 in order to provide the functionality described herein. In this simplified form, where the relay interface it utilized as a backup power source, the connector 242 includes a plurality of contact or connector pins that are adapted to be received in mating ports of consumer electronic devices. Such connectors 242 include, without limitation, USB connectors and mini USB connectors. In further arrangements, the connectors may be adapted for receipt within specialized ports of specific consumer electronic devices. For instance, Apple® products typically have specialized ports that may require, in addition to a specialized connection, a proprietary chip that allow for communicating with the electronic device. It will be appreciated in the present embodiment that the connector may include such third party hardware to allow interconnection to specific consumer electronic devices. In any arrangement, first and second pins within the connector are connected to mating electrical contacts of the consumer electronic device that connect to the power source therein. Accordingly, these pins may provide electrical power to the power control circuitry 220.

Typically, when interconnected to a consumer electronic device, power received from that consumer electronic device via the connector will be DC power. It will be appreciated that in order to transmit the power transcutaneously, that power must be converted to an alternating current (e.g., AC power). Accordingly, the power control circuitry 220 includes an inverter that allows for converting the DC power to AC power. Further, the power control circuitry may further include voltage regulators or power converters that allow for modulating, for example, voltage levels received from the consumer electronic device to a voltage that is acceptable by the implanted hearing instrument. In this regard, the power control circuitry is operative to receive a first electrical signal from the consumer electronic device and provide a second electrical signal to the implanted hearing instrument where the second electrical signal is in a form that is compatible with the implanted hearing instrument.

In another arrangement, the relay interface 200 further includes a controller 224 that permits data communication between the consumer electronic device 150 and the implanted medical device 100. See FIG. 3B. In this arrangement, the controller 224 may be programmed to provide functionality that allows communication between these devices. In this regard, the controller 224 may be in operative communication with electronic storage media 226, which may store logic or protocol that allows the controller to receive signals from one of the devices and provide signals to the other device. Typically, the relay interface 200 will include protocols for both the implanted medical device and one or more consumer electronic devices that allow for converting signals received from one of these devices into a form that is compatible with the other device.

One or more of these elements can include instructions that are stored on storage media. The instructions can be retrieved and executed by a processing system. Further, portions or such instructions may be implemented as software, hardware and/or firmware. Some examples of storage media are memory devices and integrated circuits. The instructions are operational when executed by the processor/controller to direct the system to operate in accordance with functionality described herein. The term processor or controller refers to a single processing device or group of inter-operational processing devices. Some examples of processing systems are integrated circuits and logic circuitry. Those skilled in the art are familiar with instructions processing systems and storage media.

Figure 3C:
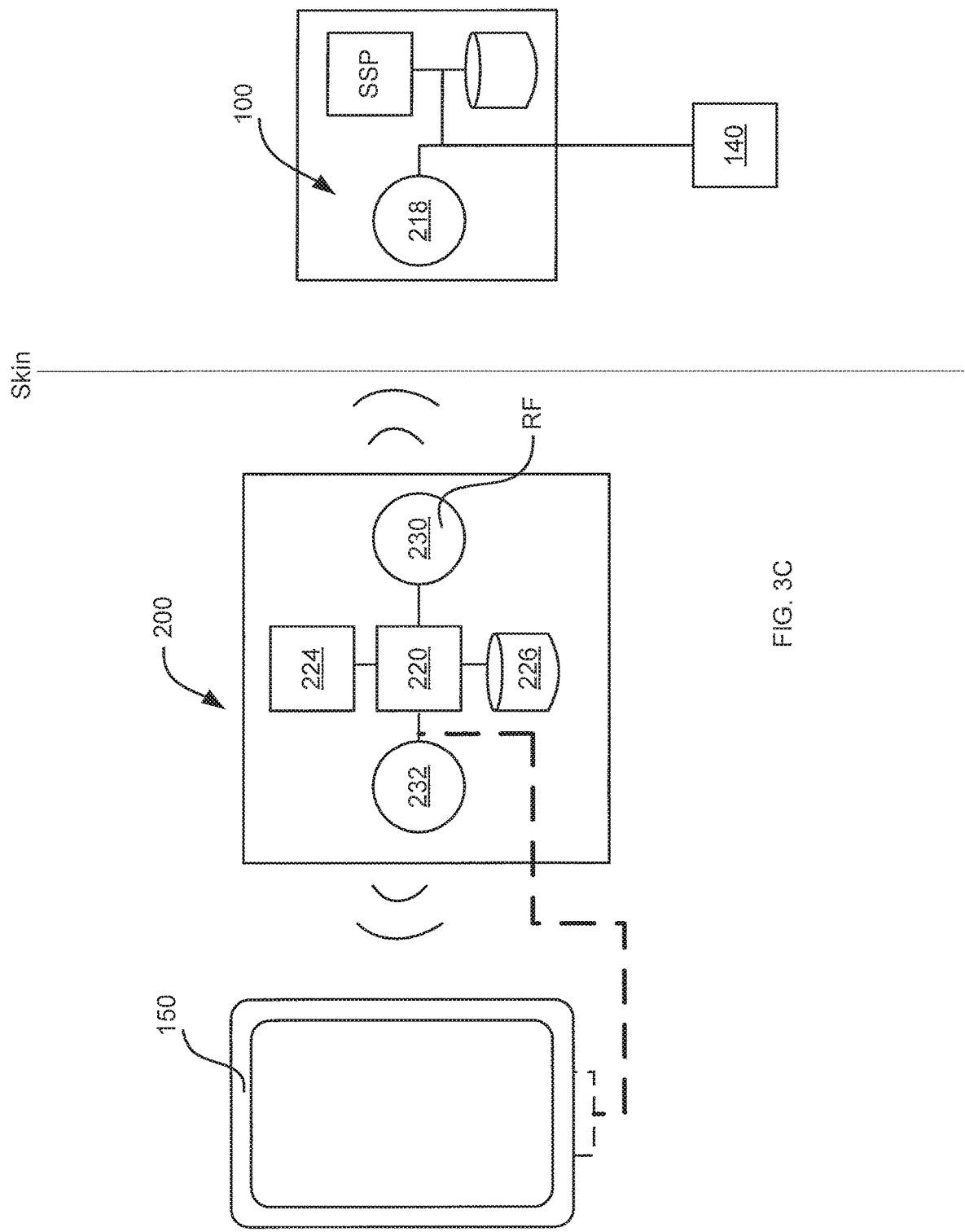
FIG. 3C illustrates a wireless relay interface.

In a yet further arrangement, a wireless relay interface is provided that is adapted for remote RE interconnection (e.g., several feet or meters) with the implanted medical device. See FIG. 3C. This arrangement utilizes an RE connection rather than an inductive coupling, which typically requires a coupling element adapted for proximate transcutaneous positioning with the implanted medical device. Accordingly, both the RE relay device and the implanted medical device include RF receivers and transmitters (e.g., transceivers) 230, 218, respectively. It will be appreciated that ability to remotely connect with a RE transceiver in the implanted medical device reduces or eliminates the ability to provide power to the implanted device from a consumer electronics device. However, the wireless relay interface 200 still permits data communication between the consumer electronic device 150 and the implanted medical device 100.

The wireless relay interface may be connected to a port of the consumer electronics device (e.g., plug in) or may communicate with the consumer electrics device via a second wireless interface 232. That is, the wireless relay interface may wirelessly communicate with both the implanted medical device 100 and the consumer electronics device 150. Again, a controller 224 within the wireless relay interface will be operative to access protocols for both the implanted medical device and one or more consumer electronic devices to allow conversion of signals received from one of these devices into a form that is compatible with the other device.

The relay interfaces may include further components as well. For instance, when utilized for purposes of fitting an implanted hearing instrument, the relay interfaces may include tone generators and/or speakers (not shown) that allow these devices to generate ambient output signals for use in a fitting procedure. Likewise, these devices may themselves include a power source that may provide backup power for an implanted medical device.

The ability to interconnect a consumer electronic device to the implantable hearing instrument utilizing a relay interface provides numerous advantages. For instance, many consumer electronic devices include a graphical user interfaces and/or input means that permit for inputting information to the consumer electronic device, which may be provided to the implanted medical device. Likewise, these graphical user interfaces may be utilized to provide instructions to users or technicians that are adjusting the medical devices. Accordingly, to provide such interface functions, the consumer electronic device 150 will typically include a specialized application that allows for communication with the relay interface and a specific implanted medical device. Furthermore, such an application may also allow for the consumer electronic device to provide information received from the implanted medical device to a communications network. Such communications network may include, without limitation, telephony networks as well as data networks. Further, such data networks may include local networks as well as wide area networks and/or internet. In this regard, a consumer electronic device may be utilized to send information received from the medical device to a remote platform for processing. Alternatively, the consumer electronic device 150 may be utilized to download information from a remote platform/location for provision to the implanted medical device.

Fitting Application

In the case of implanted hearing instruments, individual fitting of the hearing instrument is typically required. Such fitting often necessitates an audiologist applying various audio inputs to a hearing instrument and adjusting the various settings of that instrument. In this regard, the speech signal processing of the implanted hearing instrument (e.g., algorithms therein) may be altered to provide improved hearing for a specific individual. Furthermore, such algorithms may be updated from time to time as new or improved processing methods are generated. Accordingly, as new algorithms or alterations for existing algorithms are developed, it is desirable to update such hearing instruments. Typically, this has required a patient to visit an audiologist who specializes in fitting the specific implanted hearing instrument. Use of the relay interface that allows for interconnecting the implanted hearing instrument to a remote processing platform may streamline this operation.

Historically, audiologists have been provided with updated fitting parameters and/or updated algorithms as they have been become available. This process relied on the audiologist to ensure that the latest revisions or versions of such fitting parameters/algorithms are utilized. However, experience has shown that many audiologists do not maintain up-to-date databases. Accordingly, some patients may not receive the latest revisions for their implanted devices.

A further problem with current fitting procedures is that the algorithms that generate fitting parameters for the implanted hearing instrument are typically very computationally intensive. In this regard, it is not uncommon for a desktop computer to require anywhere from 2 to 15 minutes to process information received from an implanted hearing instrument in order to generate new more optimal fitting parameters for that instrument; simplified fittings are often performed to fit schedules rather than patients. In such an arrangement, after the audiologist applies various audio stimulation and receives these parameters, the audiologist and the patient are required to wait while the new fitting parameters are generated. Due to the time required to generate the parameters, the doctor and patient often lack the patience to perform multiple fitting iterations.

It has been recognized that by processing fitting algorithms at a remote location various efficiencies may be achieved. For instance, communication over a network allows for providing test parameters obtained from a patient to a remote location (e.g., network platform) that may be maintained by, for example, the maker of the implantable device. In this regard, the remote platform may have the latest up-to-date algorithms. Furthermore, such a network platform may be designed to provide high-speed processing of the test data parameters/samples/responses obtained from a patient. In this regard, test parameters received an implanted hearing instrument in response to applied audio stimuli are typically small data files. For instance, during fitting a patient may move their head in various different postures (i.e., 4 to 5 different postures) prior to receiving an audio input signal/tone. A sample and/or user response is taken at each posture. Such samples may include the response of the implanted hearing instrument to the audio input signal, which may be collected using the relay interface. Such samples and responses have very small sizes sometimes on the order of a few kbytes per sample and may be efficiently transferred to a remote server via a data network. However, the remote server may utilize multiple processors to process complex fitting algorithms in view of the received data samples/responses. For instance, such a remote server may utilize a graphics processing unit (GPU) that utilizes multiple parallel processing paths to reduce the processing time for a data set. Accordingly, the processing times for processing a data set and generating fitting information may be reduced from a few minutes to a few seconds or less, including transfer time over the data network. In this regard, the patient and the doctor are more likely to tolerate multiple iterations of fitting to determine more optimal fitting parameters for a particular patient.

Figure 4:
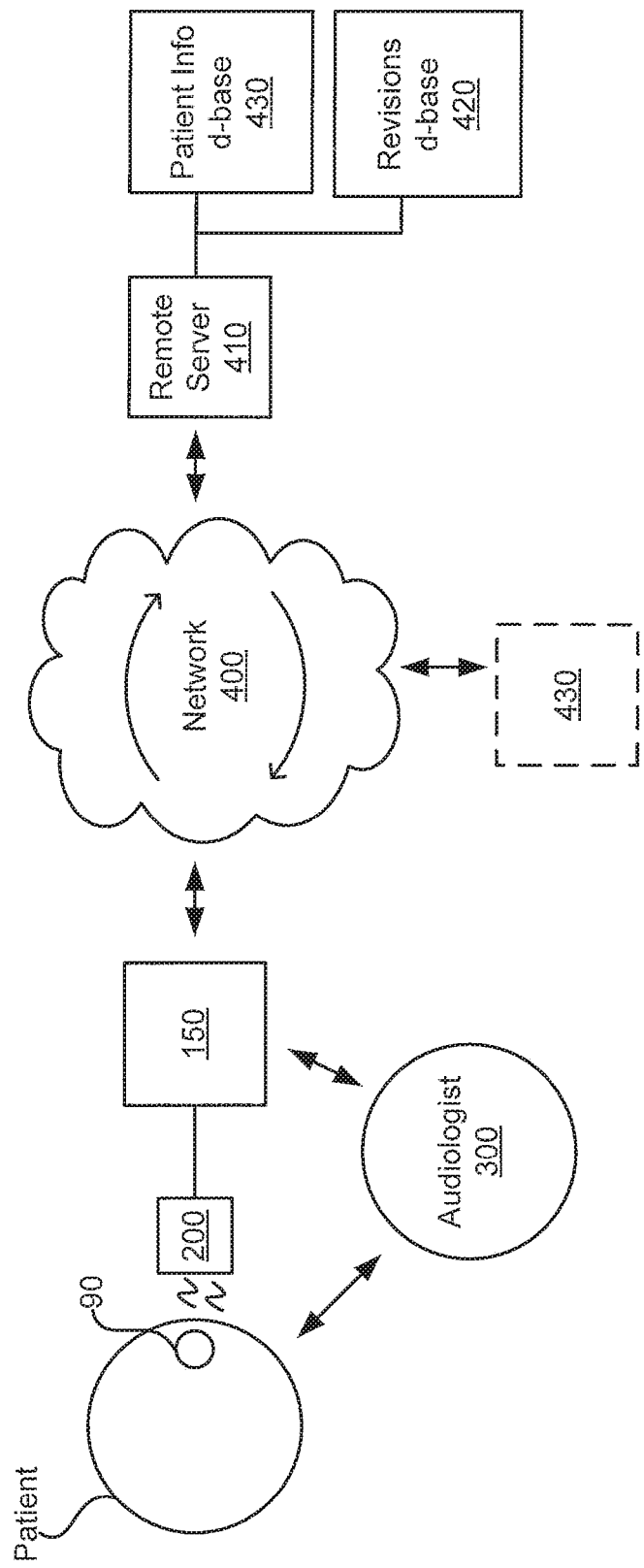
FIG. 4 illustrates a first embodiment of using a relay interface to interconnect an implanted hearing instrument to a remove platform via a network connection.

FIG. 4 illustrates one embodiment with such a system. As shown, in this embodiment, a patient having an implanted hearing instrument 90 and an audiologist 300 may be located at a common location (e.g., a doctor's office). In such an arrangement, the patient or audiologist may provide the relay interface 200 that allows for the implantable hearing instrument 90 to be interconnected to a consumer electronic device 150 such as, for example, an iPhone®, tablet computer or other devices interconnectable to the data network 400. In this arrangement, the consumer electronic device 150 may provide communication between the implanted hearing instrument and a remote server 410 that includes updated revisions 420 and processing capability. Further, such a remote server may include patient databases 430 that include, for example, information specific to individual patients. Alternatively, patient databases 430 may be located at other network accessible locations and/or reside with the audiologist. In any case, information from previous fittings may be available to the audiologist during a fitting procedure. In such an arrangement, the audiologist may apply predetermined audio stimulus to the patient to obtain data samples for transmission to the remote server as discussed above. Furthermore, the audiologist may receive new fitting parameters from the remote server 410 and, via the consumer electronic device 150 and provide these updated fitting parameters to the implanted hearing instrument 100 via the relay interface 200.

Figure 5:
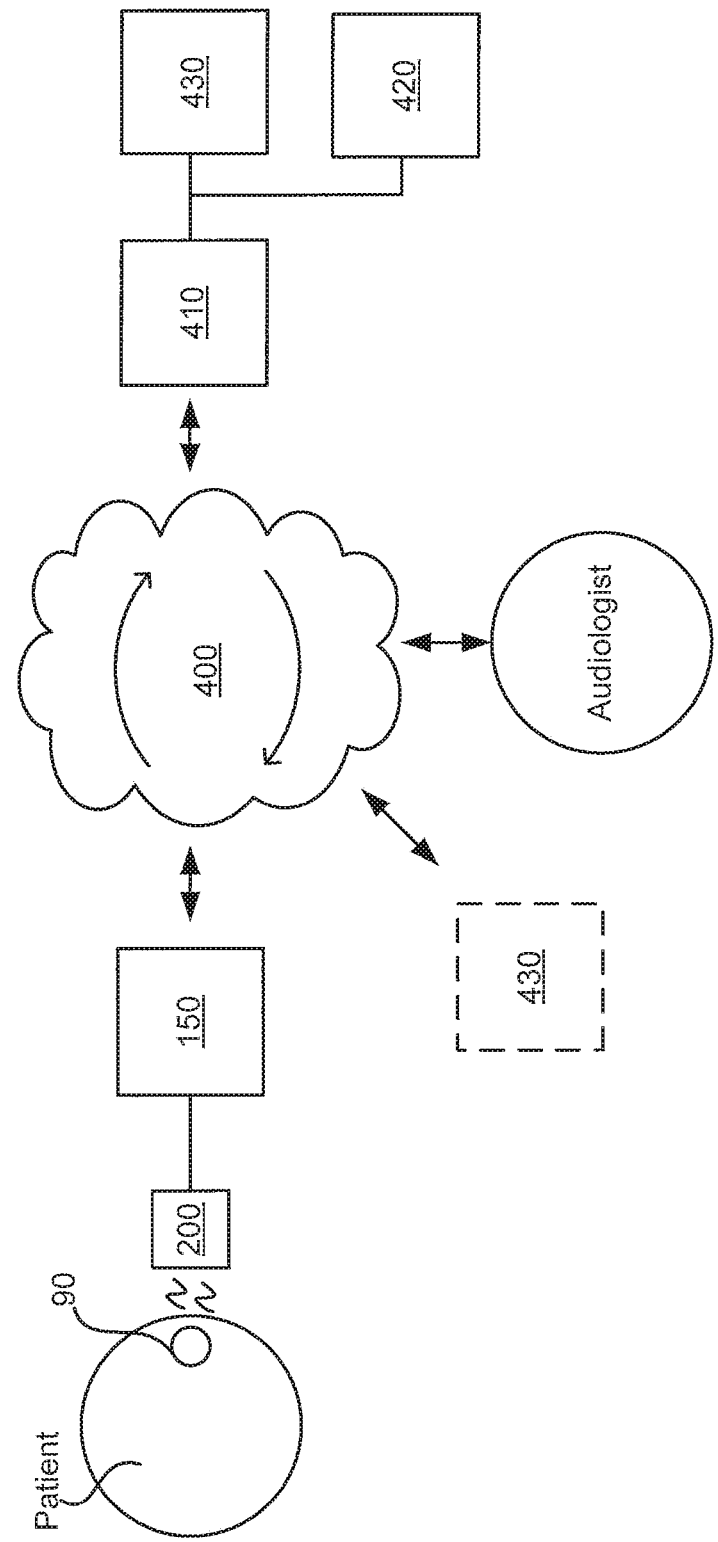
FIG. 5 illustrates a second embodiment of using a relay interface to interconnect an implanted hearing instrument to a remove platform via a network connection.

FIG. 5 illustrates an alternate embodiment. In this embodiment, the audiologist 300 may be removed from the location of the implant user. In this regard, the audiologist may be located at the location of the network platform or at a third location. In such an arrangement, a specially trained audiologist may be available to provide fittings to users of an implantable hearing instrument via a network interface. In such an arrangement, the patient/user may connect the relay interface 200 to the consumer electronic device 150, establish communication between the relay interface 150 and implanted hearing instrument 90, and establish communication with the audiologist 300 and/or remote server 410 over a data network 400.

Figure 6:
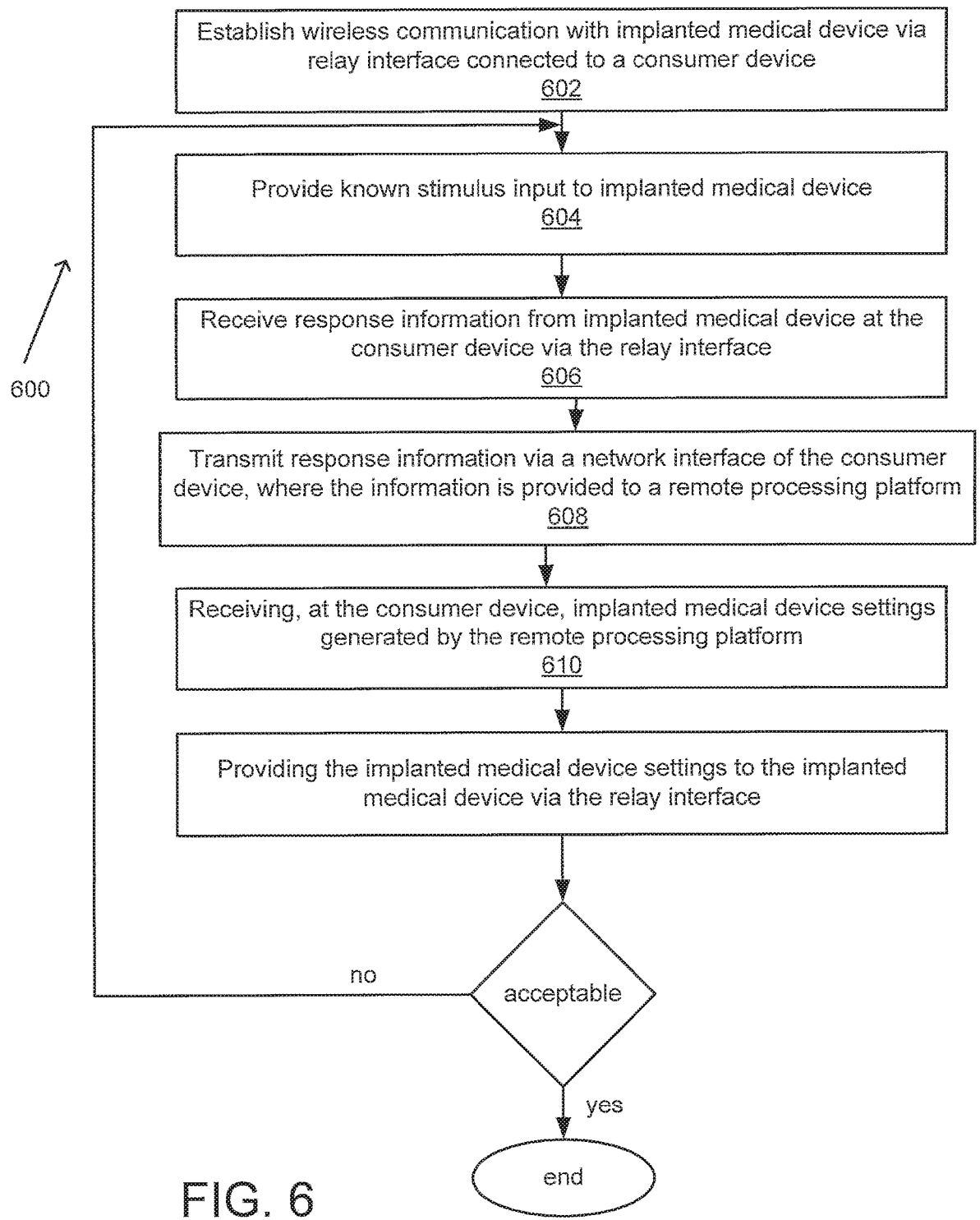
FIG. 6 illustrates one process for fitting an implanted medical device utilizing a relay interface and remote processing platform/server.

FIG. 6, in conjunction with either of FIGS. 4 and 5, provides a general overview of the fitting process 600. The fitting process 600 includes establishing 602 wireless communications with the implanted hearing instrument 90 via a relay interface 200, which is connected to a consumer electronics device 150. As noted, such wireless communication may include RF communication as well as inductive coupling. Once communication between the devices is established, a known stimulus input may be provided 604 to the implanted hearing instrument. Such known stimulus inputs may include one or more tones and/or ambient audio signals. Response information is received 606 from implanted hearing instrument 90 at the consumer electronic device 150 via the relay interface 200. Upon receiving this response information, the response information may be transmitted 608 to a remote processing platform/server 410 via a network interface 400. The remote processing platform 410 utilizes the response information and typically the input signals to determine fitting parameters for the implanted hearing attachment 90. Accordingly, the process includes receiving 610 at the consumer device medical device settings/fitting parameters generated by the remote processing platform 410. Once the fitting parameters are received via the network interface, they are provided 612 to the implanted medical device 90 via the relay interface 200. Accordingly, the controller within the implanted hearing instrument 90 may utilize the fittings to update its internal settings. At this point, a determination may be made as to whether the current fittings are acceptable. If not, the process may be repeated until the patient and/or audiologist is satisfied with the fitting.

Figure 7:
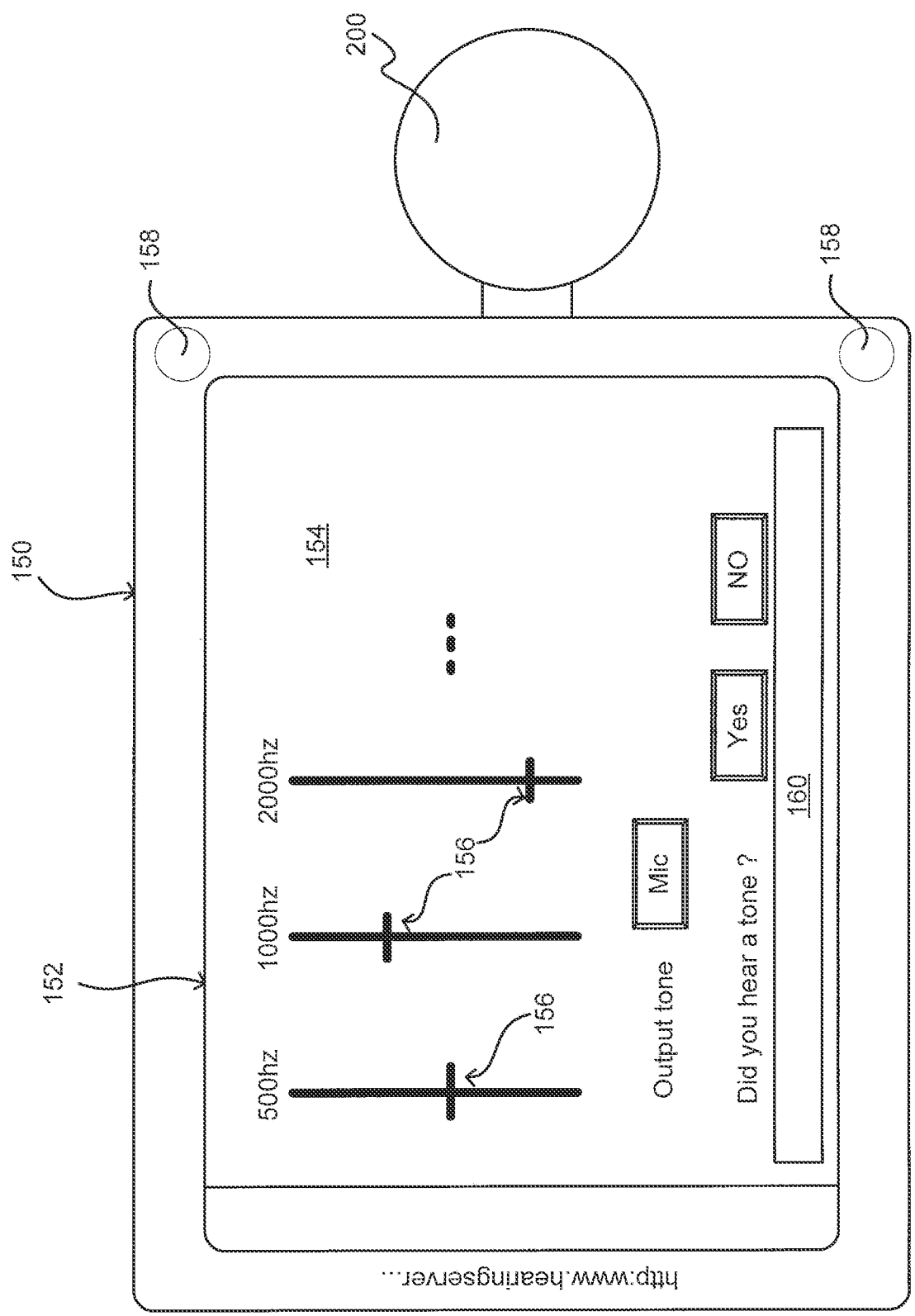
FIG. 7 illustrates one exemplary graphical user interface of a consumer electronics device that supports and application for communication with an implanted medical device and a remote processing platform/server.

In fitting applications, it may be beneficial that the consumer electronic device 150 provide a graphical user interface that allows for the user to receive instructions and/or input information. Such a system is illustrated in FIG. 7 where a consumer electronic device 150 (e.g., smart phone, tablet computer etc.) provide to display screen 152 onto which a fitting application 154 may be displayed. As shown, the consumer electronic device 150 is interconnected to the implanted hearing instrument (not shown) via an RE relay interface 200. However, this is not a requirement. In the present embodiment, the consumer electronic device 150 also includes various microphones 158 that permit the output of one or more audio tones/signals. Accordingly, these audio signals may provide inputs for use in the fitting process.

In various arrangements, the fitting application 154 may be supported/stored on the consumer electronic device 150 or may be supported via a remote server as a webpage. As shown, the application 154 may permit the selective adjustment of different frequency ranges (e.g., 500 Hz, 1000 Hz etc.) utilizing, for instance, slide adjustors 156. Other fitting parameters may likewise be adjusted. In addition to permitting the adjustment of one or more fitting parameters, the application may permit the output of testing tones/signals. As may be appreciated, various test signals, such as speech intelligibility databases and audio environments, that generate audio signals for fitting and testing purposes may be of considerable size. In some cases, these programs require over a gigabyte of storage. The present system also permits streaming of test signals from the remote platform. That is, instead of storing the signal generation program locally, the outputs of the program may be streamed to the consumer electronic device via the network. The consumer electronics device may include storage (e.g., a buffer) to allow temporary storage of this information prior to desired output as a testing signal.

The fitting application 154 also includes various user controls that permit the user or audiologist to control fitting (e.g., output tones) and/or input responses that may be sent to the remote server. For instance, where the consumer electronic device 150 is a mobile phone, a speaker of that phone may be utilized to provide audio stimulation to the user. Further, in arrangements where the audiologist is remotely located from the patient, a message bar within the graphical user interface may permit communication between the audiologist and the user. In this regard, the remote audiologist may request that the user assume various postures prior to applying an audio input signal. Once the user is correctly positioned, they may initiate the tone, for instance, via the touch screen of the device. Such an arrangement may allow users to access specifically trained audiologist who have expertise in fitting and thereby provide improved fitting for the user.

The ability of a user to receive fittings remotely may provide several additional benefits. For instance, a user may be fit for a particular environment. That is, rather than being fit while in an audiologists office, a user may be fit in an audio environment where, for instance, a certain level of background noise is present (e.g., a work environment). In this regard, a particular fitting of the implanted hearing instrument may be more optimized for a specific use. Likewise, the ability to remotely access a patient database 430, may also permit a user to remotely store a plurality of fittings that may be prepared for differing settings. By way of example only, a user may store fittings for high noise environments, low noise environments, specialized environments such as concerts/listening to music, and/or for enhancing speech intelligibility. The remote storage various fittings for differing environments may allow a user to access and download a particular fitting based on their current needs, Stated otherwise, a user may change between predetermined fittings based on their needs. Further, if updated algorithms are developed, these stored fittings may be automatically updated. In addition to pre-stored fittings, a user may also have the ability to adjust various settings of their hearing instrument. In this regard, a user may be provided an adjustment interface (see e.g., FIG. 7) and may be permitted to change values of the hearing instrument setting. In such an arrangement, constraints such as pre-determined limits may be placed on the settings to prevent the user from placing a setting outside of an acceptable boundary.

Another benefit of the remote processing capabilities provided by the presented systems is the potential accumulation of data/parameters from multiple medical devices. As will be appreciated, there may be instances where patients having similar underlying conditions and utilize a common implanted medical device having similar settings. New patients having the same or similar underlying conditions may benefit from use similar settings. In this regard, it may be beneficial during a fitting or other adjustment, to provide an initial set of fitting parameters based on similarly situated patients. That is, in another aspect, fittings/parameters of different patients may be accumulated to provide fitting/ parameters suggestions for new patients or patients being fit for a specific purpose.

Figure 8:
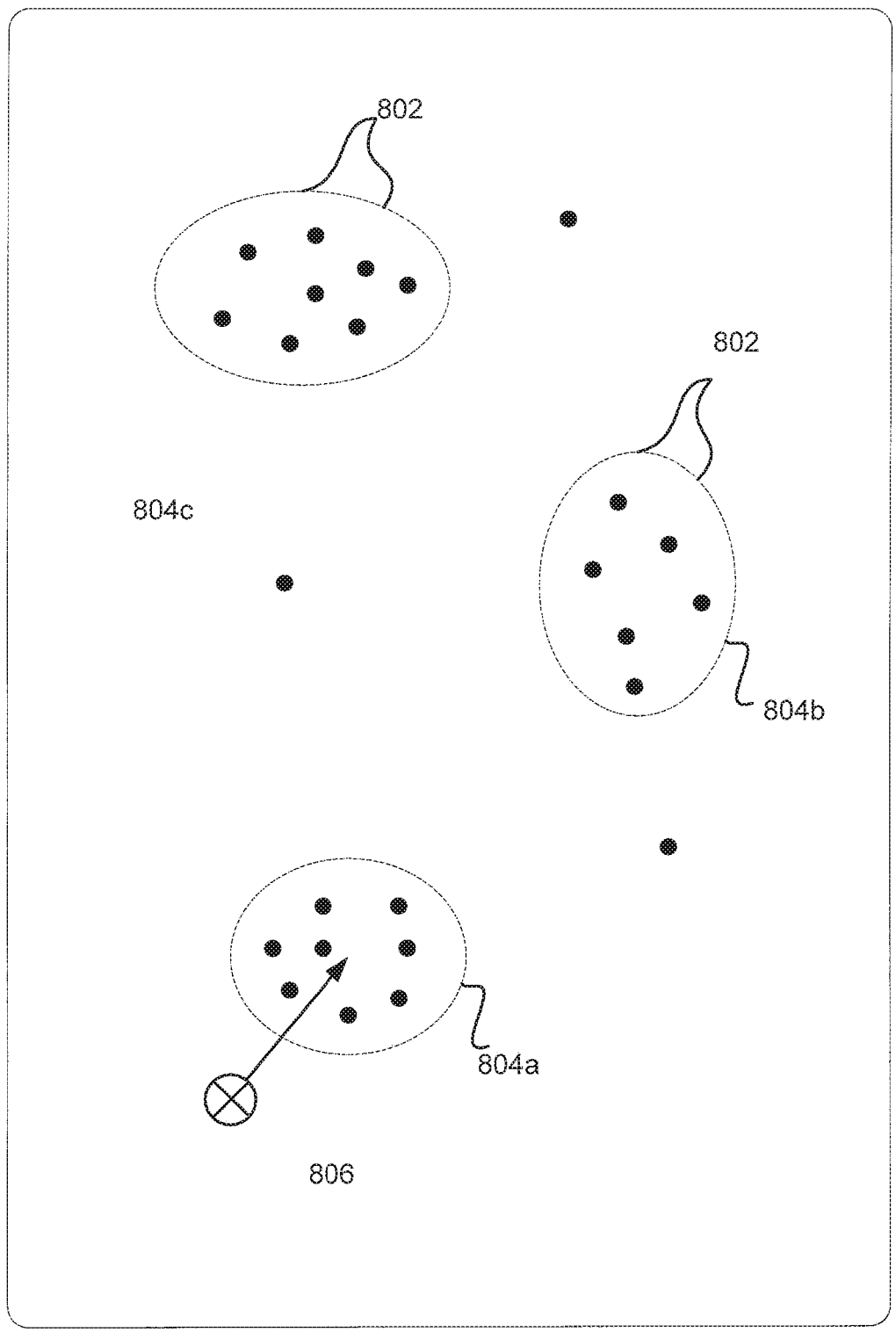
FIG. 8 illustrates mapping a plurality of fitting parameters to a multi-dimensional space.

FIG. 8 graphically illustrates an n-dimensional space where successful fittings 802 are indexed against one or multiple variables. For instance, in the case of hearing instruments it will be appreciated that different patients may have different types of hearing loss. Some patients have 'notch-loss' hearing loss where a narrow frequency band within the frequency range of hearing is impaired. Such loss may result from overstimulation in a narrow frequency range (e.g., gun shots, etc). Other patients may have high-frequency or low frequency hearing loss where hearing loss progressively worsens as frequencies increase or decrease, as the case may be. Further, multiple fittings and associated settings may be generated for such patients (e.g., noisy environments, listening to music, speech intelligibility, etc.). Use of an n-dimensional space allows for plotting or mapping successful fittings 802 utilized by actual patients against a multitude of differing variables (type of loss, type of environment, etc). Likewise, fitting of new patients may be facilitated by comparison to such accumulated data. Of course, such information/data may be scrubbed of any information that could identify an individual patient.

As shown in FIG. 8, it may be expected that upon generating a large database of parameters/fitting 802, which may be received via a data network, various generalities may be identified. For instance, neural networks or other data processing systems may identify trends within the data. As illustrated in FIG. 8 by way of example and not limitation, the plotting of various different hearing fittings 802 in an n-dimensional space may result in the identification of separate clusters 804*a-n* having one or more similarities. When a new patient requests a fitting or adjustment, initial fitting parameters and/or responses of a patient may be plotted into or otherwise compared to the n-dimensional space using well-known method of multivariate statistical analysis. As shown, the initial response 806 is located proximate to one of the identified clusters 804*a*. Based on this proximity, the processing platform may suggest fitting parameters that are closer to or an average of the fittings 802 within the cluster 804*a*. Alternatively, conditions of the patient (e.g., notch hearing loss between 2-3 kHz) and/or intended environment may be compared with similarly situated patients and initial settings may be selected based on successful fittings of similarly situated patients. In this latter regard, users may provide inputs (keywords etc.) or be provided with input prompts that allow for matching them with similarly situated users.

Figure 9:
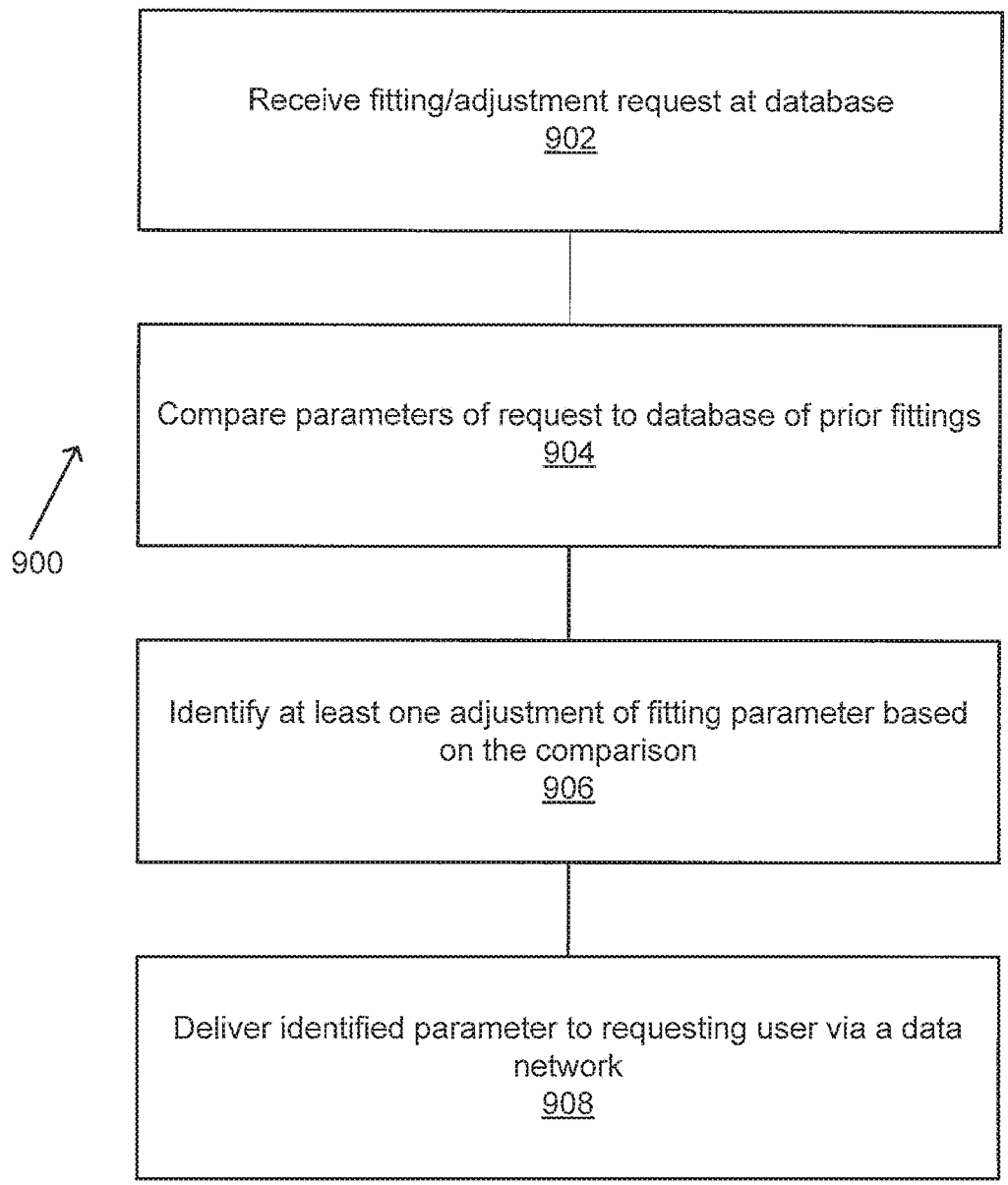
FIG. 9 illustrates one process for providing suggested fitting parameters based on statistical fitting parameters.

FIG. 9 illustrates a process 900 for use in providing adjustment/fitting parameters. Initially, a request for fitting parameters is received 902 via a data network. This request may include patient information identifying the type of hearing loss and or other information about the patient. In addition and/or alternatively, the request may include a response of an implanted medical device/hearing aid to known stimulus. In any arrangement, the parameters received by the network are compared 904 to a database of prior adjustment/fitting parameters. Based on this comparison, one or more fitting and/or adjustment parameters are identified 906 for use with the implanted medical device/ hearing instrument. Accordingly, these adjustment/fitting parameters may be provided 908 to the implanted medical device via the data network. As will be appreciated, provision of this information may include provision to a graphical display of consumer electronics device interconnected to the implanted medical device. In this regard, a user or medical technician may implement such adjustments. Alternatively, these adjustment/fitting parameters may be provided directly to the implanted medical device via the consumer electronics device and relay interface to allow for automated adjustment of the implanted medical device in accordance with the parameters.

In general, the use of a remote server allows for accumulating information associated with multiple fittings and providing suggested fittings based on this information. How this information is categorized is a matter of design choice; well known examples include clustering, nearest neighbor, self-organizing maps, support vector machines, kernel method, and other statistical learning methods, What is important is that a current patient may be compared to previous successful parameters to identify suggested parameters. Of course, such suggested parameters may be altered once received. However, provision of such initial setting may significantly reduce the fitting time.

Remote Microphone

In a further arrangement, the ability to interconnect the implanted hearing instrument 90 to a consumer electronic device 150 using the relay interface 200 may allow for utilizing that consumer electronic device 150 as an audio input to the hearing instrument 90. As will be appreciated, many consumer electronic devices such as mobile phones/ smart phones include sophisticated microphones. By interconnecting the relay interface to such a phone and utilizing an appropriate application on that phone, the phone may temporarily replace, for example, an implanted microphone of the hearing instrument as the input source for the hearing instrument. This may allow, for example, the user of the hearing instrument to position the consumer electronic device at a desired location (e.g., center of a table) to improve hearing functionality. Further, the application that permits use of the consumer electronics device/phone as an input microphone may provide filtering or other signal processing functions to the implant device.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The invention claimed is:

1. A method, comprising:
obtaining access to a sensory prosthesis to be fitted to a recipient and/or to be adjusted;
obtaining data based on people from a database; and
fitting and/or adjusting the prosthesis based on the obtained data, wherein
the people are recipients of respective sensory prostheses, and
the data based on people is associated with information regarding a type of hearing loss of the recipients utilizing the prostheses.

2. The method of claim 1, wherein:
the database contains accumulated data/parameters related to multiple prostheses, and the obtained data relates to such.

3. The method of claim 2, wherein:
the action of fitting and/or adjusting includes fitting, wherein the fitting results in an initial set of fitting parameters of the prosthesis, wherein the method includes, during the action of fitting, subsequently adjusting parameters of the prosthesis from the initial set of fitting parameters.

4. The method of claim 3, wherein:
the prosthesis to which access is obtained is common to a prosthesis of the multiple prostheses, and the obtained data relates to the prosthesis of the multiple prostheses.

5. The method of claim 1, wherein:
the data based on similarly situated recipients is data that corresponds to accumulated information from the respective sensory prosthesis.

6. The method of claim 1, wherein:
the action of fitting and/or adjusting the prosthesis is executed by a user or technician located at a common location as the prosthesis.

7. The method of claim 1, wherein:
the action of fitting and/or adjusting the prosthesis is executed by a user or technician remote from the location of the prosthesis.

8. The method of claim 1, wherein:
the database is multivariate database.

9. The method of claim 1, further comprising:
obtaining information relating to the recipient and/or a current response of the sensory prosthesis; and
utilizing the obtained information when obtaining the data based on people from the remote database, wherein
the fitting and/or adjusting is executed using fitting parameters/settings identified and/or suggested based on the obtained data.

10. The method of claim 1, further comprising:
the obtained data based on similarly situated recipients is data that was developed by comparing information relating to the recipient and/or the sensory prosthesis to a dataset of recipients of sensory prostheses, wherein the comparison was a multivariate statistical analysis.

11. The method of claim 1, wherein:
the database is multivariate database; and
the obtained data upon which the fitting and/or adjusting of the prosthesis is based is based on a multivariate statistical analysis of data in the database.

12. A method, comprising:
obtaining access to a sensory prosthesis to be fitted to a recipient and/or to be adjusted;
obtaining data based on people from a database; and
fitting and/or adjusting the prosthesis based on the obtained data, wherein
the people are recipients of respective sensory prostheses, and
the data based on people is associated with information regarding types of environment of use of the prostheses by recipients of the prostheses,
the database is a multivariate database; and
the obtained data upon which the fitting and/or adjusting of the prosthesis is based is data that is based on a multivariate statistical analysis of data stored in the database.

13. The method of claim 12, wherein:
the fitting and/or adjustment is an initial fitting and/or adjustment of the prosthesis based on similarly situated people.

14. The method of claim 12, wherein:
the obtained data is based on accumulated fitting/parameters of different people;
the method further comprises providing a fitting/parameters suggestion for the recipient; and
the obtained data is the suggestion.

15. The method of claim 12, wherein:
the sensory prosthesis of the recipients are of the same type as the accessed sensory prosthesis.

16. The method of claim 12, further comprising:
accumulating information from the respective sensory prosthesis and storing this information in a location accessible via a data network such that this information may be utilized in subsequent fitting and/or adjustment of such prostheses, the accumulated information corresponding to the data based on people from the remote database remote from the prosthesis.

17. The method of claim 12, wherein:
the data based on people is information associated with settings of prostheses.

18. The method of claim 12, further comprising:
obtaining data relating to the prosthesis, wherein
the obtained data based on similarly situated recipients is data that is also based on the obtained data relating to the prosthesis.

19. The method claim 12, further comprising:
uploading the obtained data to the prosthesis to fit and/or adjust the prosthesis.

20. The method claim 12, further comprising:
obtaining fitting and/or setting parameters based on the obtained data; and
uploading the parameters to fit and/or adjust the prosthesis.

21. The method of claim 12, wherein:
the obtained data upon which the fitting and/or adjusting of the prosthesis is based is settings of prostheses.

22. The method of claim 12, wherein:
the environment is one or more of noise, music or intelligibility of speech.

23. A method for use with a sensory prosthesis, comprising:
obtaining access to a sensory prosthesis;
establishing data communication between the sensory prosthesis and consumer electronics device having a network interface connectable to a database;
utilizing the consumer electronics device, obtaining data based on people from the database; and fitting and/or adjusting the prosthesis based on the obtained data, wherein the people are recipients of respective sensory prostheses, the data based on people is associated with information regarding types of environment of use of the prostheses by recipients of the prostheses and/or a type of hearing loss of the recipients utilizing the prostheses, and if the data is associated with information regarding types of environment of use of the prosthesis by recipients, the database is a multivariate database, and if the data is associated with information regarding types of environment of use of the prosthesis by recipients, the obtained data used to fit and/or adjust the prosthesis is data that is based on a multivariate statistical analysis of data stored in the database.

24. The method of claim 23, wherein:

the data based on people are parameters to fit and/or adjust the prosthesis, and the method further comprises:

transmitting the received parameters to the sensory prosthesis; and storing the transmitted parameters in the sensory prosthesis to fit and/or adjust the prosthesis.

25. The method of claim 23, further comprising:

obtaining data relating to a recipient of the sensory prosthesis, wherein the obtained data is obtained based at least in part on the obtained data relating to the recipient, and the data based on people is a result of a fitting algorithm executed using the obtained data relating to the recipient.

26. The method of claim 23, wherein:

the consumer electronics device is a smart phone, a computer or a tablet.

* * * * *